(12) United States Patent
Oikawa et al.

(10) Patent No.: US 7,161,036 B2
(45) Date of Patent: Jan. 9, 2007

(54) PROCESS FOR PRODUCING OXIME

(75) Inventors: Miyuki Oikawa, Niihama (JP); Masami Fukao, Ritto (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/014,812

(22) Filed: Dec. 20, 2004

(65) Prior Publication Data
US 2005/0137423 A1 Jun. 23, 2005

(30) Foreign Application Priority Data
Dec. 22, 2003 (JP) .............................. 2003-424582

(51) Int. Cl.
*C07C 249/04* (2006.01)
(52) U.S. Cl. ..................................................... 564/253
(58) Field of Classification Search ................ 564/267
See application file for complete search history.

(56) References Cited

U.S. PATENT DOCUMENTS

| 4,745,221 A |   | 5/1988 | Roffia et al. |
| 4,954,325 A |   | 9/1990 | Rubin et al. |
| 5,498,793 A | * | 3/1996 | Mantegazza et al. ....... 564/265 |
| 5,736,479 A | * | 4/1998 | Schodel et al. ............... 502/77 |
| 6,114,551 A |   | 9/2000 | Levin et al. |
| 6,288,004 B1 | * | 9/2001 | Balducci et al. .............. 502/85 |
| 6,462,235 B1 | * | 10/2002 | Thiele et al. ................ 564/253 |

FOREIGN PATENT DOCUMENTS

| EP | 0496385 A1 |   | 7/1992 |
| JP | 6-92922 A |   | 4/1994 |
| JP | 2000-72737 A |   | 3/2000 |
| JP | 2000072738 | * | 3/2000 |
| WO | WO-03/074421 A1 |   | 9/2003 |

OTHER PUBLICATIONS

English language abstract of JP 2000 072737 A (Mar. 7, 2000).
Wu et al., "Hydrothermal synthesis of a novel titanosilicate with MWW topology", Chemistry Letters, No. 7, 2000, pp. 774-775.

* cited by examiner

*Primary Examiner*—Thorman K. Page
*Assistant Examiner*—Chukwuma Nwaonicha
(74) *Attorney, Agent, or Firm*—Birch, Stewart, Kolasch & Birch, LLP

(57) ABSTRACT

A process for producing an oxime is provided, wherein the process comprises the step of reacting a ketone, hydrogen peroxide and ammonia in the presence of a crystalline titanosilicate having MWW structure under the condition that the ammonia concentration in the liquid portion of the reaction mixture is about 1% by weight or more. By the process, an ammoximation reaction of the ketone can be carried out with a high conversion of the ketone and a high selectivity to the oxime corresponding to the ketone, thereby producing the oxime with a high yield.

6 Claims, No Drawings

PROCESS FOR PRODUCING OXIME

BACKGROUND OF THE INVENTION

1. Field of the Invention

The present invention relates to a process for producing an oxime by the ammoximation reaction of a ketone. An oxime is useful as a raw material of an amide or a lactam, etc.

2. Description of the Related Art

For producing an oxime, one of proposed methods is that ammoximation of a ketone is conducted with hydrogen peroxide and ammonia using as a catalyst titanosilicate (see, Japanese Unexamined Patent Application Publication No. (JP-A-) 62-59256, JP-A-6-49015 and JP-A-6-92922), particularly using a crystalline titanosilicate having MFI structure (such as titanium silicalite TS-1 disclosed in JP-A-56-96720). It is also known that a specified crystalline titanosilicate having MWW structure is utilized as a catalyst for ammoximation reaction (see, International Publication No. 03/074421).

SUMMARY OF THE INVENTION

The above-described conventional methods, however, do not necessarily give a sufficient conversion of a ketone and a sufficient selectivity to an oxime in some cases. One of the objects of the present invention is to provide a process for producing an oxime with a high yield, by carrying out ammoximation of ketone with a high conversion of ketone and a high selectivity to oxime.

The present inventors have intensively studied and have consequently found that the object can be achieved by conducting an ammoximation reaction of a ketone using, as a catalyst, a crystalline titanosilicate having MWW structure, in a preferable concentration of ammonia in the liquid portion of the reaction mixture. The present invention has been accomplished based on the findings.

The present invention provides a process for producing an oxime, the process comprising the step of reacting a ketone, hydrogen peroxide and ammonia in the presence of a crystalline titanosilicate having MWW structure under the condition that the ammonia concentration in the liquid portion of the reaction mixture is about 1% by weight or more.

In accordance with the present invention, an ammoximation reaction of a ketone can be carried out with a high conversion of the ketone and a high selectivity to the oxime corresponding to the ketone, thereby producing the oxime with a high yield.

DESCRIPTION OF THE PREFERRED EMBODIMENTS

A catalyst utilized in ammoximation reaction in the present invention comprises a crystalline titanosilicate having MWW structure. (Hereinafter, a crystalline titanosilicate having the MWW structure is sometimes referred to as a "Ti-MWW".) The symbol "MWW" is one of the structural codes of zeolite which are defined by International Zeolite Association (IZA), as with the aforementioned symbol "MFI". In addition, the term "titanosilicate" means a species containing titanium, silicon and oxygen as the elements constituting its framework, and may have the framework substantially made from titanium, silicon and oxygen, or may have the framework containing optional elements such as boron, aluminum, gallium, iron and chromium, in addition to titanium, silicon and oxygen.

A structure having MWW structure can be confirmed by X-ray diffraction analysis (see, for example, U.S. Pat. No. 4,954,325; Chemical Communications, No. 10, pp. 897–898, 2001, Britain; etc.). Being titanosilicate can be ensured by ultraviolet visible absorption spectrum analysis. Specific examples of compounds having the MWW structure include MCM-22, SSZ-25, ITQ-1, ERB-1, PSH-3 and the like.

The Ti-MWW suitably utilized in the present invention may contains titanium in the concentration of about 0.05% by weight to about 10% by weight, and may have the atomic ratio of silicon to titanium being from 10 to 1000. The shape of the Ti-MWW may be, for example, a fine powder form or a pellet form.

The Ti-MWW can be produced by processes which are roughly classified into direct synthesis processes and post synthesis processes. The direct synthesis processes are methods which comprise using a titanium compound at a first stage in the form of gel as one of starting materials, and then heating and calcining the resulting mixture to conduct crystallization thereof. Examples of the direct processes include (i) a hydrothermal synthesis method using a silicon compound and a titanium compound as starting materials (see, Chemistry Letters, No. 7, pp. 774–775, 2000, etc.); and (ii) a dry gel conversion method using a silicon compound and a titanium compound as starting materials (see, Proceedings of the 88th Catalyst Symposium A, p. 154, 2001, etc.). The post synthesis processes are methods which comprise once preparing a crystalline silicate having the MWW structure free of titanium and then introducing titanium thereto. Examples of the post synthesis processes include (iii) a method which comprises preparing a crystalline aluminosilicate having the MWW structure, removing the aluminum therefrom and subsequently incorporating titanium thereto (see, U.S. Pat. No. 6,114,551, etc.); and (iv) a method which comprises preparing a crystalline borosilicate having the MWW structure, removing the boron therefrom, breaking the crystal structure, introducing titanium thereto, and then conducting crystallization again (see, Catalyst, Vol. 44, No. 6, pp. 468–470, 2002; International Publication No. 03/074421, etc.). Among these methods, the methods of the above-described (i), (ii) and (iv) wherein the crystallization is conducted in the presence of titanium, since titanium can readily be introduced even into the inside of the crystal.

In the present invention, an oxime is produced in the presence of a Ti-MWW by reacting a ketone, hydrogen peroxide and ammonia, i.e., carrying out the ammoximation of the ketone with hydrogen peroxide and ammonia. During the ammoximation reaction, the Ti-MWW is preferably present as a solid thereof in the resulting reaction mixture while being suspended in the mixture. Namely, the reaction mixture is preferably composed of a solid Ti-MWW and a liquid portion of the mixture. The amount of the suspended Ti-MWW may be in the range of from about 0.1% by weight to about 10% by weight based on the liquid portion.

The ketone, a starting material, maybe an aliphatic ketone, or an alicyclic ketone, or an aromatic ketone. As required, two or more species thereof may be employed. Examples of the ketone include dialkyl ketones such as acetone, ethyl methyl ketone and isobutyl methyl ketone; alkyl alkenyl ketones such as mesityl oxide; alkyl aryl ketones such as acetophenone; diaryl ketones such as benzophenone; cycloalkanones such as cyclopentanone, cyclohexanone, cyclooctanone and cyclododecanone; cycloalkenones such as cyclopentenone and cyclohexenone; and the like. Among these ketons, cycloalkanones are preferred in the present invention.

The ketone, a starting material, may be obtained, for example, by oxidation of an alkane, by oxidation (dehydrogenation) of a secondary alcohol, or by hydration and oxidation (dehydrogenation) of an alkene.

Hydrogen peroxide is typically produced by the so-called anthraquinone process, and is commercially available as an aqueous solution having a concentration of 10% by weight to 70% by weight, which can be used for the present invention. The amount of hydrogen peroxide to be used may be in the range of from about 0.5 mole to about 3 moles, and is preferably in the range of from about 0.5 mole to about 1.5 moles, based on one mole of the ketone to be reacted therewith. The hydrogen peroxide may contain, for example, a stabilizer including a phosphate such as sodium phosphate, a polyphosphate such as sodium pyrophosphate and sodium tripolyphosphate, pyrophosphoric acid, ascorbic acid, ethylene diamine tetraacetic acid, nitrotriacetic acid, aminotriacetic acid, and diethylene triamine pentaacetic acid.

The ammonia to be used in the present invention may be in the gas state, or in the liquid state, or in a solution of water or of an organic solvent. The amount of ammonia to be used is determined appropriately depending on the amount of liquid portion of the reaction mixture, so that the ammonia concentration in the liquid portion of the reaction mixture is about 1% by weight or more. Such an ammonia concentration in the liquid portion of a reaction mixture to be in the preferable range improves the conversion of a ketone, i.e., a starting material, and also the selectivity to an oxime, i.e., a target material, which results in improvement of the yield of an oxime that is a target material. The concentration of ammonia in the liquid portion of the reaction mixture is more preferably about 1.5% by weight or more; and may be about 10% by weight or less, and is preferably about 5% by weight or less. The amount of ammonia may be, as a measure (rough standard), about one (1) mole or more, and is preferably about 1.5 moles or more, based on one mole of the ketone to be reacted.

The ammoximation reaction may be carried out in a solvent. Preferable examples of the solvents include alcohols such as methyl alcohol, ethyl alcohol, n-propyl alcohol, isopropyl alcohol, n-butyl alcohol, s-butyl alcohol, t-butyl alcohol and t-amyl alcohol, and water. In particular, a mixture solvent of an alcohol and water is preferably used.

The ammoximation reaction may be carried out by batch operation, or continuous operation. The reaction is preferably carried out by continuous operation while supplying a ketone, hydrogen peroxide and ammonia to the reaction system, and removing the liquid portion of the resulting reaction mixture out of the reaction system. Such a continuous operation is preferred in terms of productivity and operativity.

The batch reaction may be carried out, for example, by placing a ketone, ammonia, a Ti-MWW and a solvent in a reaction vessel and introducing hydrogen peroxide thereinto while agitating; or by placing a ketone, a Ti-MWW and a solvent in a reaction vessel and introducing hydrogen peroxide and ammonia thereinto while agitating; or by placing a Ti-MWW and a solvent in a reaction vessel and introducing a ketone, hydrogen peroxide and ammonia thereinto while agitating.

The continuous reaction can favorably be carried out, for example, by a method comprising the steps of preparing a Ti-MWW suspension mixture in a reaction vessel, and supplying a ketone, hydrogen peroxide and ammonia thereinto, while removing the liquid portion of the resulting reaction mixture through a filter out of the reaction vessel. The reaction vessel is preferably a glass lined vessel or a stainless steel vessel, from the viewpoint of preventing the hydrogen peroxide from decomposing.

The reaction temperature of the ammoximation reaction may be in the range of from about 50° C. to about 100° C., and is preferably in the range of from about 70° C. to about 100° C. The reaction may be carried out at normal atmospheric pressure or higher. In order to make the ammonia easily dissolve in the liquid portion of the reaction mixture, the reaction is preferably conducted under pressurized conditions by a pressure in the range of from 0.2 MPa to about 1 MPa in terms of the absolute pressure (over normal atmospheric pressure), and is more preferably in the range of from about 0.2 MPa to about 0.5 MPa. In this case, the pressure may be controlled using an inert gas such as nitrogen or helium.

The post treatment procedure of the resultant reaction mixture is appropriately selected. For instance, the post treatment procedure can be conducted by separating the Ti-MWW from the reaction mixture by filtration, decantation, or the like, and then distilling the liquid portion to separate the obtained oxime.

The invention being thus described, it will be apparent that the same may be varied in many ways. Such variations are to be regarded as within the spirit and scope of the invention, and all such modifications as would be apparent to one skilled in the art are intended to be within the scope of the following claims.

The entire disclosure of the Japanese Patent Application No. 2003-424582 filed on Dec. 22, 2003, indicating specification, claims and summary, are incorporated herein by reference in their entirety.

EXAMPLE

The present invention is described in more detail by following Examples, which should not be construed as a limitation upon the scope of the present invention.

In Examples and Comparative Example, cyclohexanone and cyclohexanone oxime were analyzed by gas chromatography. Based on the results, the conversion of cyclohexanone, the selectivity to cyclohexanone oxime and the yield of cyclohexanone oxime were calculated, respectively.

Example 1

A continuous reaction was carried out under the pressurized conditions of a temperature of 85° C., an added pressure of 0.35 MPa (in terms of absolute pressure) and a residence time of 72 minutes by supplying to a one liter capacity autoclave as a reaction vessel, 67 g per hour of cyclohexanone, 260 g per hour of water-containing t-butyl alcohol (water: 12% by weight) and 44.7 g per hour of 60% by weight of hydrogen peroxide, and also supplying ammonia so that the ammonia is present in a concentration of 2% by weight in the liquid portion of the reaction mixture, while removing the liquid portion of the reaction mixture through a filter out of the reaction vessel. During this period of reaction, a Ti-MWW (which had been prepared in accordance with the method described in International Publication No. 03/074421) was made to be present in a concentration of 1% by weight based on the liquid portion in the reaction mixture in the reaction vessel. In 1.5 hours after the reaction initiation, the liquid portion was analyzed. As a result, a conversion of cyclohexanone was 96.2%, a selectivity to cyclohexanone oxime was 99.5%, and a yield of cyclohexanone oxime was 95.7%.

Example 2

A similar procedure was carried out in the same manner as in Example 1, except that another Ti-MWW, which had been prepared by the method described in Chemistry Letters, No. 7, pp. 774–775, 2000, was employed. As a result, a conversion of cyclohexanone was 97.0%, a selectivity to cyclohexanone oxime was 99.6% and a yield of cyclohexanone oxime was 96.6%.

Comparative Example 1

A similar procedure was carried out in the same manner as in Example 1, except that a TS-1 (which had been prepared by the method described in JP-A-56-96720) instead of using the Ti-MWW in Example 1. As a result, a conversion of cyclohexanone was 87.3%, a selectivity to cyclohexanone oxime was 97.2% and a yield of cyclohexanone oxime was 84.8%.

What is claimed is:

1. A process for producing an oxime, the process comprising the step of reacting a ketone, hydrogen peroxide and ammonia in the presence of a crystalline titanosilicate having a MWW structure, under the reaction condition that ammonia concentration in a liquid portion of the reaction mixture is about 1% by weight or more.

2. A process according to claim 1, wherein the reaction is carried out while supplying the ketone, hydrogen peroxide and ammonia to the reaction system while removing the liquid portion of the reaction mixture out of the reaction system.

3. A process according to claim 1 or 2, wherein the reaction is carried out using a solvent.

4. A process according to claim 3, wherein the solvent is a mixture of an alcohol and water.

5. A process according to claim 1 or 2, wherein the reaction is conducted under pressurized conditions by a pressure in the range of from 0.2 MPa to about 1 MPa in terms of an absolute pressure.

6. A process according to claim 1 or 2, wherein the ketone comprises a cycloalkanone.

* * * * *